US010303197B2

United States Patent
Oh et al.

(10) Patent No.: US 10,303,197 B2
(45) Date of Patent: May 28, 2019

(54) TERMINAL DEVICE INCLUDING REFERENCE VOLTAGE CIRCUIT

(71) Applicant: SAMSUNG ELECTRONICS CO., LTD., Suwon-si (KR)

(72) Inventors: Seung-hyun Oh, Seoul (KR); Woo-jin Jang, Hwaseong-si (KR); Jong-woo Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/870,252

(22) Filed: Jan. 12, 2018

(65) Prior Publication Data
US 2019/0025867 A1    Jan. 24, 2019

(30) Foreign Application Priority Data
Jul. 19, 2017    (KR) ........................ 10-2017-0091601

(51) Int. Cl.
   *G05F 3/26*       (2006.01)
   *H04B 1/40*       (2015.01)
   *A61B 5/00*       (2006.01)
(52) U.S. Cl.
   CPC ............ *G05F 3/267* (2013.01); *A61B 5/6898* (2013.01); *H04B 1/40* (2013.01)
(58) Field of Classification Search
   CPC combination set(s) only.
   See application file for complete search history.

(56) References Cited

U.S. PATENT DOCUMENTS

| 5,245,273 | A | * | 9/1993 | Greaves | ................... G05F 3/30 323/313 |
| 5,304,949 | A | * | 4/1994 | Chun | ........................ H03F 3/08 330/296 |
| 5,596,265 | A | * | 1/1997 | Wrathall | ................... G05F 3/20 323/315 |

(Continued)

FOREIGN PATENT DOCUMENTS

| CN | 105786082 A | 7/2016 |
| CN | 105955391 A | 9/2016 |

(Continued)

OTHER PUBLICATIONS

Liang, Yu et al., CN 105786082A Translation, Jul. 20, 2016 (Year: 2016).*

(Continued)

*Primary Examiner* — Nay A Maung
*Assistant Examiner* — Erica L Fleming-Hall
(74) *Attorney, Agent, or Firm* — Sughrue Mion, PLLC

(57) ABSTRACT

A reference voltage circuit is provided. The reference voltage circuit includes a first current bias circuit including a first node; a second current bias circuit including a plurality of NMOS transistors and a second node, and an amplifier configured to output a reference voltage having same value as the second voltage. The plurality of NMOS transistors include a first NMOS transistor and a second NMOS transistor, the first NMOS transistor is connected to the first node, and the plurality of NMOS transistors are connected to the second node and configured to perform a sub-threshold operation based on a first voltage of the first node so that a second voltage is generated at the second node.

20 Claims, 17 Drawing Sheets

(56) References Cited

U.S. PATENT DOCUMENTS

| | | | | |
|---|---|---|---|---|
| 6,016,051 A * | 1/2000 | Can | ............ | G05F 3/30 323/314 |
| 6,194,887 B1 * | 2/2001 | Tsukada | ................. | G05F 1/465 323/312 |
| 7,750,728 B2 | 7/2010 | Marinca | | |
| 7,843,254 B2 | 11/2010 | Chellappa | | |
| 8,461,914 B2 | 6/2013 | Shibayama | | |
| 8,542,000 B1 | 9/2013 | Youssefi | | |
| 8,791,684 B2 | 7/2014 | Lym et al. | | |
| 8,836,413 B2 | 9/2014 | Gunther et al. | | |
| 2003/0011349 A1 * | 1/2003 | Kuroiwa | ................. | G05F 3/265 323/281 |
| 2005/0140428 A1 * | 6/2005 | Tran | ........... | G05F 3/30 327/539 |
| 2006/0091875 A1 * | 5/2006 | Kimura | ..................... | G05F 3/30 323/315 |
| 2006/0181258 A1 * | 8/2006 | Benbrik | ................ | G05F 1/565 323/315 |
| 2007/0170905 A1 * | 7/2007 | Huang | ..................... | G05F 1/565 323/315 |
| 2007/0176591 A1 * | 8/2007 | Kimura | ................... | G05F 3/245 323/315 |
| 2008/0129272 A1 * | 6/2008 | Kimura | ..................... | G05F 3/30 323/315 |
| 2008/0252282 A1 * | 10/2008 | Inoue | ..................... | G05F 3/225 323/315 |
| 2008/0252364 A1 * | 10/2008 | Chou | ........................ | G05F 3/24 327/543 |
| 2009/0051343 A1 * | 2/2009 | Nagumo | ................... | G05F 3/30 323/316 |
| 2009/0121699 A1 | 5/2009 | Park et al. | | |
| 2009/0267585 A1 * | 10/2009 | Liu | ........................... | G05F 3/30 323/313 |
| 2010/0052645 A1 * | 3/2010 | Huang | ................... | G05F 1/561 323/315 |
| 2010/0072972 A1 * | 3/2010 | Yoshikawa | ............... | G05F 3/30 323/313 |
| 2011/0193544 A1 * | 8/2011 | Iacob | ..................... | G05F 3/242 323/315 |
| 2013/0147448 A1 * | 6/2013 | Kadanka | ................. | G05F 1/565 323/280 |
| 2014/0111010 A1 * | 4/2014 | Kumar | ............... | H03K 19/0008 307/31 |
| 2014/0340068 A1 * | 11/2014 | Lin | ........................... | G05F 3/26 323/313 |
| 2015/0145487 A1 * | 5/2015 | Fort | ........................ | G05F 3/30 323/265 |
| 2015/0153753 A1 * | 6/2015 | Fort | ......................... | G05F 3/30 323/282 |
| 2015/0168971 A1 * | 6/2015 | Tomioka | ................ | G05F 1/562 323/275 |
| 2015/0370280 A1 * | 12/2015 | Ryabchenkov | ........... | G05F 3/26 323/315 |
| 2016/0274616 A1 | 9/2016 | Roy | | |
| 2016/0282895 A1 | 9/2016 | Kiuchi | | |
| 2017/0060166 A1 * | 3/2017 | Shukla | ..................... | G05F 3/267 |
| 2017/0070149 A1 * | 3/2017 | Guan | ........................ | G05F 1/46 |

FOREIGN PATENT DOCUMENTS

| | | |
|---|---|---|
| JP | 2003-256056 A | 9/2003 |
| KR | 10-2013-0123903 A | 11/2013 |

OTHER PUBLICATIONS

Sheng, Wenjun et al., CN 105955391 Translation, Sep. 21, 2016 (Year: 2016).*

Yamamoto, Shinya et al., JP 200356056 Translation, Sep. 10, 2003 (Year: 2003).*

Communication dated Oct. 2, 2018 issued by the Singapore Patent Office in Counterpart Singapore Application No. 10201803548P.

* cited by examiner

TERMINAL DEVICE INCLUDING REFERENCE VOLTAGE CIRCUIT

CROSS-REFERENCE TO RELATED APPLICATION

This application claims priority from Korean Patent Application No. 10-2017-0091601, filed on Jul. 19, 2017 in the Korean Intellectual Property Office, the disclosure of which is incorporated herein by reference in its entirety.

BACKGROUND

Field

Methods and apparatuses consistent with example embodiments relate to a semiconductor device, and more particularly, to a terminal device including a reference voltage circuit driven by ultra-low power by using a sub-threshold current.

Related Art

Applications where energy consumption is a key metric have been developed. Such energy-constrained applications may require low activity rates and low speeds. Also, these applications may require a long battery life span (for example, one year or more). For example, energy consumption may be a concern for a sensor implanted in a living subject and that provides location information.

Location information provided by such a sensor may be provided to a remote device, such as a server over a communication network. The remote device may estimate a location of the living subject based on the location information provided by the sensor. In particular, when the sensor is implanted in an animal, an internal battery may provide driving power and the sensor has to be continually turned-on. Thus, a method of minimizing the driving power of the sensor is required.

SUMMARY

According to an aspect of an example embodiment, there is provided reference voltage circuit including a first current bias circuit including a first node; a second current bias circuit comprising a plurality of NMOS transistors and a second node, the plurality of NMOS transistors including a first NMOS transistor and a second NMOS transistor, the first NMOS transistor being connected to the first node, and the plurality of NMOS transistors being connected to the second node and configured to perform a sub-threshold operation based on a first voltage of the first node so that a second voltage is generated at the second node; and an amplifier configured to output a reference voltage having same value as the second voltage.

According to an aspect of another example embodiment, there is provided a terminal device including: a communicator configured to receive a first signal via a wireless communication network and transmit a second signal corresponding to the first signal via the wireless communication network; and a reference voltage circuit configured to be driven by a power voltage, generate a reference voltage and apply the reference voltage to the communicator, the reference voltage circuit including: a first current bias circuit including a first node; a second current bias circuit including a plurality of NMOS transistors and a second node, the plurality of NMOS transistors including a first NMOS transistor and a second NMOS transistor, the first NMOS transistor being connected to the first node, and the plurality of NMOS transistors being connected to the second node and configured to perform a sub-threshold operation according to a first voltage of the first node to generate a second voltage at the second node; and an amplifier configured to output the reference voltage having a same value as the second voltage.

According to an aspect of yet another example embodiment, there is provided an operating method of a terminal device, the operating method including: receiving a first signal with respect to the terminal device; performing a sub-threshold operation of at least two NMOS transistors connected between a power voltage and a ground voltage to generate a reference voltage; generating a second signal corresponding to the first signal based on the reference voltage; and transmitting the second signal.

BRIEF DESCRIPTION OF THE DRAWINGS

The above and/or other aspects will become more apparent from the following description of example embodiments taken in conjunction with the accompanying drawings in which.

DETAILED DESCRIPTION OF EXAMPLE EMBODIMENTS

Figure 1:
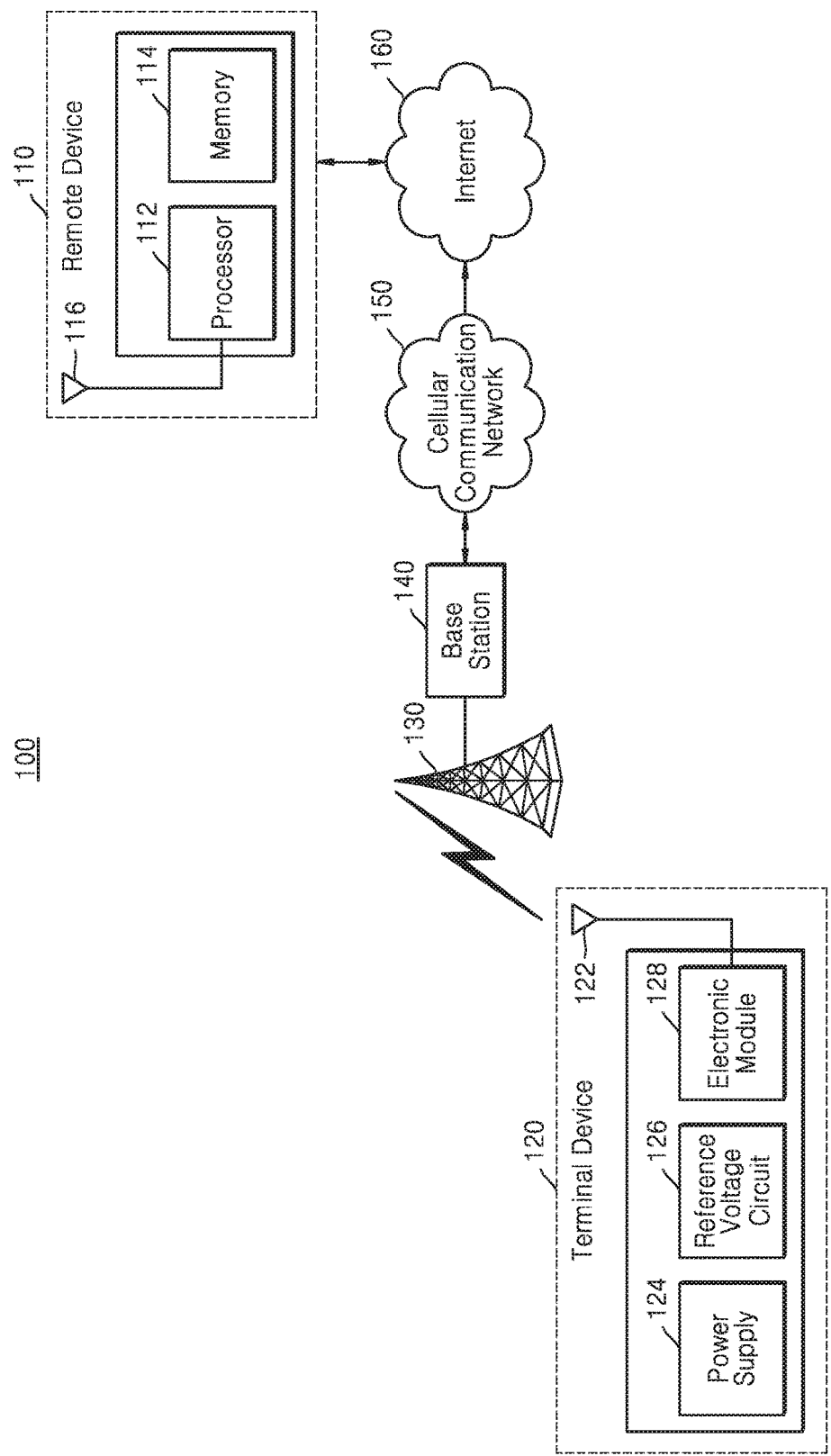
FIG. 1 is a block diagram for describing a wireless communication system according to an example embodiment.

FIG. 1 is a block diagram for describing a wireless communication system 100 according to an example embodiment.

Referring to FIG. 1, the wireless communication system 100 may include a remote device 110 and a terminal device 120. The wireless communication system 100 may allow the remote device 110 to receive a wireless signal and estimate information from the terminal device 120.

According to some example embodiments, the terminal device 120 may be implanted in a living subject, that is, a biological life form. The terminal device 120 may provide various information according to its purpose of use. For example, a location of a subject, in which the terminal device 120 is mounted, and bio signals (for example, blood pressure, temperature, changes in thoracic volume due to breathing, etc.) may be sensed and provided as information by the terminal device 120.

According to example embodiments, the terminal device 120 may also be implanted in a non-living structure (e.g., machines, buildings, etc.). The terminal device 120 may provide information with respect to a state (e.g., a location, a temperature, etc.) of the non-living structure.

The terminal device 120 may transmit a wireless signal to the remote device 110 via a wireless communication network. The wireless communication network may include a cellular communication network 150 using a cell tower 130 and a base station 140. The cellular communication network 150 may include, for example, at least one of long-term evolution (LTE), LTE-advance (LTE-A), code division multiple access (CDMA), wideband CDMA (WCDMA), a universal mobile telecommunications system (UMTS), wireless broadband (WiBro), and global system for mobile communications (GSM).

The wireless communication network between the terminal device 120 and the remote device 110 may include a short-range wireless communication network. The short-range wireless communication network may include, for example, at least one of wireless fidelity (WiFi), Bluetooth, near-field communication (NFC), and a global navigation satellite system (GNSS). The GNSS may include, for example, at least one of a global positioning system (GPS), a global navigation satellite system (Glonass), a Beidou navigation satellite system, and Galileo, the European global satellite-based navigation system.

The cellular communication network 150 may communicate with the Internet 160 accessing the remote device 110. The remote device 110 may communicate with the terminal device 120 via a computer network (e.g., a local area network (LAN) or a wide area network (WAN)) or the Internet 160. Also, the remote device 110 may access a wireless short-range communication network, such as Bluetooth, WiFi, or Zigbee, or a mobile cellular network, such as power line communication (PLC), $3^{rd}$ generation (3G), or LTE, and may perform wireless communication with the terminal device 120. The remote device 110 may receive, via an antenna 116, the wireless signal transmitted by the terminal device 120.

The base station 140 may be a fixed station communicating with the terminal device 120. The base station 140 may communicate with the terminal device 120 or other base stations and exchange various data and control information with the terminal device 120 or the other base stations. The base station 140 may be referred to as evolved-Node B (eNB), a base transceiver system (BTS), an access point, or other terms.

The terminal device 120 may be stationary or mobile and may be any device capable of communicating with the base station 140 to transmit and receive various data and control information. The terminal device 120 may be referred to as a sensor, user equipment (UE), a mobile station (MS), a mobile terminal (MT), a user terminal (UT), a subscribe station (SS), a wireless device, a handheld device, etc.

The remote device 110 may include a processor 112 and a memory 114. The processor 112 may include one or more of a central processing unit (CPU), an application processor (AP), and a communication processor (CP). The processor 112 may be operationally connected to at least one other component of the remote device 110 and may control general operations of components of the remote device 110.

The processor 112 may be referred to as a controller, a microcontroller, a microprocessor, a microcomputer, or the like. The processor 112 may be implemented as hardware, firmware, software, or a combination thereof. When the processor 112 is implemented as hardware, the processor 112 may include application specific integrated circuits (ASICs), digital signal processors (DSPs), programmable logic devices (PLDs), field programmable gate arrays (FPGAs), etc.

When the processor 112 is implemented as firmware or software, the firmware or the software may be configured to include modules, procedures, functions, etc., performing functions or operations of the processor 112. The firmware or the software may be installed in the processor 112 or stored in the memory 114 to be driven by the processor 112.

The memory 114 may temporarily or permanently store various information of the remote device 110. The memory 114 may store programs for processing or controlling the processor 112 and may store information that is input and output. Also, the memory 114 may be used as a buffer. The memory 114 may be implemented as flash memory, a hard disk, a MultiMediaCardmicro (MMCmicro), a card (for example, an SD card or XD memory), random access memory (RAM), static random access memory (SRAM), read-only memory (ROM), electrically erasable programmable read-only memory (EEPROM), programmable read-only memory (PROM), magnetic memory, a magnetic disk, an optical disk, or the like.

According to example embodiments, the remote device 110 may operate in connection with a web storage that performs a storage function of the memory 114 on the Internet 160.

The remote device 110 may process information with respect to the terminal device 120, based on the wireless signal transmitted by the terminal device 120. For example, the remote device 110 may obtain a location (or a local location) of the terminal device 120, and may allow the processor 112 to calculate data with respect to the location and store the calculated data in the memory 114. Further, the processor may analyze the stored calculated data to estimate a motion of the terminal device 120.

The terminal device 120 may include an antenna 122, a power supply 124, a reference voltage circuit 126, and an electronic module 128. The terminal device 120 may perform wireless communication with the cellular communication network 150 in a predetermined manner, via the cell tower 130 and the base station 140. For example, the terminal device 120 may be triggered to perform data communication with the cellular communication network 150, based on various triggers. The triggers may include a timer, a real time clock, an event, a trigger signal received from the cellular communication network 150, etc.

The antenna 122 may be mounted for wireless communication. The antenna 122 may receive information, data, signals, messages, or trigger signals from the outside. The antenna 122 may be referred to as an antenna port. The antenna port may correspond to one physical antenna or may include a combination of a plurality of physical antennas.

The power supply 124 may supply power to the components included in the terminal device 120. The power supply 124 may include a battery, and the battery may include an embedded battery. For example, the battery may include any one of a lead storage battery, an alkaline battery, a gas cell, a lithium-ion battery, a nickel-hydride battery, a nickel-cadmium cell, a polymer battery, and a lithium polymer battery. However, the battery is not limited thereto.

According to example embodiments, the terminal device 120 may receive solar heat and convert the received solar heat into electrical energy.

The reference voltage circuit 126 may generate a reference voltage $V_{REF}$ by using a band gap of silicon. The terminal device 120 may recognize an external trigger signal based on the reference voltage $V_{REF}$, and output information thereof to an external device in response to the external trigger signal.

To reduce power consumption, the terminal device 120 may recognize external trigger signals by maintaining a standby state at all times without large power consumption. For example, the terminal device 120 may include an ultra-low-power sensor which requires dozens of microwatts (μW) or a few hundred nanowatts (nW).

The reference voltage circuit 126 may generate the reference voltage $V_{REF}$ based on a sub-threshold operation from among operation models of N-channel metal oxide semiconductor (NMOS) transistors. The reference voltage circuit 126 may include a plurality of NMOS transistors and may be designed such that the NMOS transistors perform a sub-threshold operation. The sub-threshold operation may be performed under a condition in which a gate-source voltage $V_{GS}$ of the NMOS transistors is biased to be lower than a threshold voltage Vth of the NMOS transistors ($V_{GS} \leq Vth$), and a drain-source voltage $V_{DS}$ of the NMOS transistors is biased to be higher than 0 V ($V_{DS} > 0$).

When the NMOS transistors perform the sub-threshold operation, the sub-threshold operation is performed with a very low voltage and a very low current. Power consumed during the sub-threshold operation of the NMOS transistors is, for example, almost equal to power consumed by normally-off logic gates. Accordingly, the reference voltage circuit 126 may have ultra-low power consumption and may be suitable for use in the terminal device 120 having ultra-low power consumption.

The electronic module 128 may transmit the information of the terminal device 120 to the outside via the antenna 122, by using the reference voltage $V_{REF}$ generated by the reference voltage circuit 126. The electronic module 128 may include a wireless communication circuit, such as a mobile chip-set radio frequency (RF) wireless circuit or a cellular radio. The electronic module 128 may establish a link with an external wireless device and transmit and receive information to and from the external wireless device. The electronic module 128 may perform, via the link, a data transmission control operation, such as a timing control operation and an RF control operation, with respect to the external wireless device.

Figure 2:
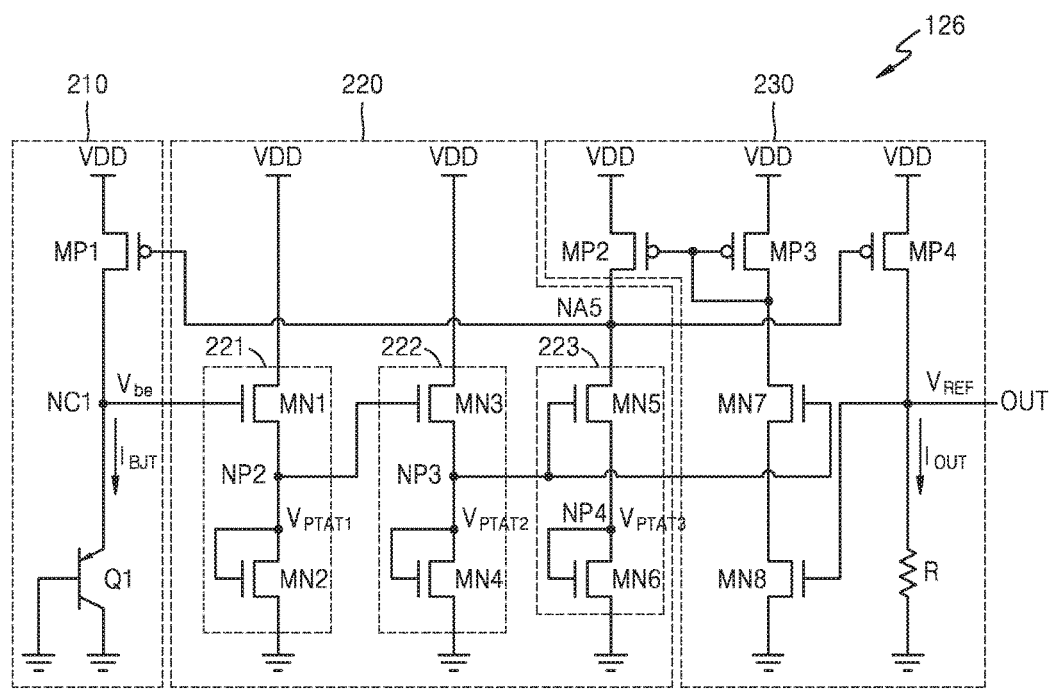
FIG. 2 is a circuit diagram for describing a reference voltage circuit of FIG. 1 according to an example embodiment.

FIG. 2 is a circuit diagram for describing the reference voltage circuit 126 of FIG. 1 according to an example embodiment.

Referring to FIG. 2, the reference voltage circuit 126 may be driven via a power voltage VDD, which may be provided from the power supply 124 (refer to FIG. 1), and may generate a reference voltage $V_{REF}$ having a value substantially the same as a band gap (for example, 1.205 V) of silicon. The reference voltage circuit 126 may include a first current bias circuit 210, a second current bias circuit 220, and an amplifier 230.

The first current bias circuit 210 may use a bipolar transistor Q1 to generate a first voltage $V_{be}$ according to a first current $N_{bjt}$. The first current bias circuit 210 may include a PNP bipolar transistor Q1 and a first P-channel metal oxide semiconductor (PMOS) transistor MP1.

Both a base and a collector of the PNP bipolar transistor Q1 may be connected to a ground voltage VSS, and an emitter of the PNP bipolar transistor Q1 may be connected to a first node NC1 so as to form a diode-connected bipolar transistor. The first PMOS transistor MP1 may include a source, to which a power voltage VDD is connected, a gate, to which a fifth node NA5 of the second current bias circuit 220 is connected, and a drain, to which the first node NC1 is connected. The first node NC1 is connected to the emitter of the PNP bipolar transistor Q1 and the drain of the PMOS transistor 212.

An operation of the PNP bipolar transistor Q1 may be schematically represented by Equation 1 and Equation 2 below.

$$I_{bjt} = I_S \left( e^{qVbe/kT} - 1 \right) \quad \text{[Equation 1]}$$

$$V_{be} = \frac{kT}{q} \ln \frac{I_{bjt}}{I_S} \quad \text{[Equation 2]}$$

Here, k is Boltzmann's constant, q is a charge of an electron, T is an operation temperature according to the Kelvin temperature scale, $I_s$ is a saturation current, and $N_{bjt}$ is an emitter current.

A forward-biased base-emitter voltage $V_{be}$ of the PNP bipolar transistor Q1 has a temperature dependent characteristic. That is, the forward-biased base-emitter voltage $V_{be}$ of the PNP bipolar transistor Q1 has a complementary to absolute temperature (CTAT) voltage characteristic, whereby a voltage decreases as a temperature increases.

In Equation 2, kT/q denotes a thermal voltage $V_T$. The thermal voltage $V_T$ increases as a temperature increases. However, the saturation current $I_s$ increases by a much greater percentage than the terminal voltage $V_T$, and thus, the base-emitter voltage $V_{be}$ of the PNP bipolar transistor Q1 may have the CTAT voltage characteristic. The base-emitter voltage $V_{be}$ of the PNP bipolar transistor Q1 is a voltage of the first node NC1 of the first current bias circuit 210 and may be provided to the second current bias circuit 220.

Figure 3:
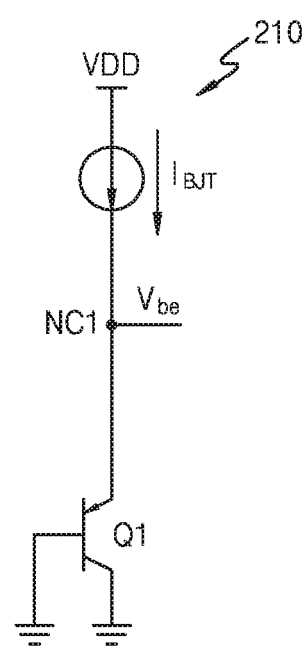
FIG. 3 is a diagram for modeling a first current of FIG. 2 according to an example embodiment.

An emitter current of the PNP bipolar transistor Q1 is the first current $N_{bjt}$ and is the same as a drain current of the first PMOS transistor MP1. The drain current of the first PMOS transistor MP1 may have the same value as an output current $I_{out}$ of the amplifier 230. That is, the drain current of the first PMOS transistor MP1 may be determined by receiving a feedback of an operational result of the amplifier 230. Accordingly, in the first current bias circuit 210, the first PMOS transistor MP1 (FIG. 2) may be modelled as a current source 310 corresponding to the first current $I_{bjt}$, as illustrated in FIG. 3.

The second current bias circuit 220 of FIG. 2 may include first through third sub-threshold operation circuits 221 through 223 including a plurality of NMOS transistors MN1 through MN6. The second current bias circuit 220 may be designed such that the NMOS transistors MN1 through MN6 perform a sub-threshold operation by the base-emitter voltage $V_{be}$ of the PNP bipolar transistor Q1, the base-emitter voltage $V_{be}$ being the voltage of the first node NC1 of the first current bias circuit 210. Also, the second current bias circuit 220 may be designed such that a voltage obtained as a result of the sub-threshold operation of the NMOS transistors MN1 through MN6 has a same value as the reference voltage $V_{REF}$ output by the amplifier 230.

Figure 15:
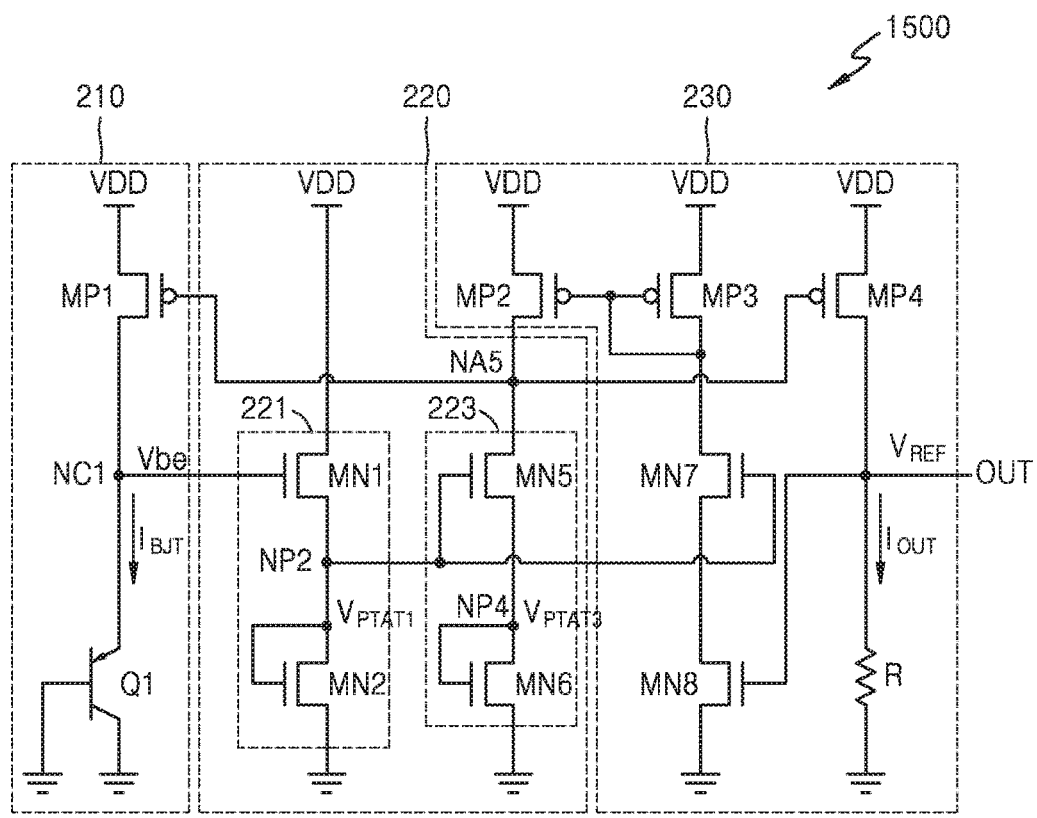

According to the present example embodiment, it is described that the second current bias circuit 220 includes the three sub-threshold operation circuits 221 through 223. However, example embodiments are not limited thereto, and the second current bias circuit 220 may include various numbers of sub-threshold operation circuits. For example, the second current bias circuit 220 may include one subthreshold operation circuit 221 (FIG. 16) or two sub-threshold operation circuits 221 and 222 (FIG. 15).

The first sub-threshold operation circuit 221 may include the first and second NMOS transistors MN1 and MN2 connected in series between the power voltage VDD and the ground voltage VSS. The first NMOS transistor MN1 may include a drain, to which the power voltage VDD is connected, a gate, to which the first node NC1 of the first current bias circuit 210 is connected, and a source, to which a second node NP2 is connected. The second NMOS transistor MN2 may include a gate and a drain, to which the second node NP2 is connected, and a source, to which the ground voltage VSS is connected.

The base-emitter voltage $V_{be}$ of the PNP bipolar transistor Q1 of the first node NC1 may be applied to the gate of the first NMOS transistor MN1. Thus, a gate-source voltage $V_{GS}$ of each of the first and second NMOS transistors MN1 and MN2 is biased to be lower than a threshold voltage Vth of each of the first and second NMOS transistors MN1 and MN2 ($V_{GS} \leq $Vth). Also, a drain-source voltage $V_{DS}$ of each of the first and second NMOS transistors MN1 and MN2 is biased to be higher than 0 V ($V_{DS}>0$). Accordingly, each of the first and second NMOS transistors MN1 and MN2 may perform a sub-threshold operation from among operation models of the NMOS transistors.

The second sub-threshold operation circuit 222 may include the third and fourth NMOS transistors MN3 and MN4 connected in series between the power voltage VDD and the ground voltage VSS. The third NMOS transistor MN3 may include a drain, to which the power voltage VDD is connected, a gate, to which the second node NP2 is connected, and a source, to which a third node NP3 is connected. The fourth NMOS transistor MN4 may include a gate and a drain, to which the third node NP3 is connected, and a source, to which the ground voltage VSS is connected.

A voltage $V_{PTAT1}$ of the second node NP2 may be applied to the gate of the third NMOS transistor MN3. The voltage $V_{PTAT1}$ of the second node NP2 is lower than the voltage $V_{be}$ of the first node NC1 inducing the sub-threshold operation of the first and second NMOS transistors MN1 and MN2. Thus, a gate-source voltage $V_{GS}$ of each of the third and fourth NMOS transistors MN3 and MN4 is biased to be lower than a threshold voltage Vth of each of the third and fourth NMOS transistors MN3 and MN4 ($V_{GS} \leq $Vth). Also, a drain-source voltage $V_{DS}$ of each of the third and fourth NMOS transistors MN3 and MN4 is biased to be higher than 0 V ($V_{DS}>0$). Accordingly, each of the third and fourth NMOS transistors MN3 and MN4 may perform a sub-threshold operation.

The third sub-threshold operation circuit 223 may include the fifth and sixth NMOS transistors MN5 and MN6 connected in series. The fifth NMOS transistor MN5 may include a drain, to which a fifth node NA5 of the amplifier 230 is connected, a gate, to which the third node NP3 is connected, and a source, to which a fourth node NP4 is connected. The sixth NMOS transistor MN6 may include a gate and a drain, wherein the fourth node NP4 is connected to the gate and the drain, and a source, to which the ground voltage VSS is connected. The third node NP3 and the fourth node NP4 may operate as symmetrical nodes in comparison to a connection structure in the amplifier 230.

A voltage $V_{PTAT2}$ of the third node NP3 may be applied to the gate of the fifth NMOS transistor MN5. The voltage $V_{PTAT2}$ of the third node NP3 is lower than the voltage $V_{PTAT1}$ of the second node NP2 inducing the sub-threshold operation of the third and fourth NMOS transistors MN3 and MN4. Thus, a gate-source voltage $V_{GS}$ of each of the fifth and sixth NMOS transistors MN5 and MN6 is biased to be lower than a threshold voltage Vth of each of the fifth and sixth NMOS transistors MN5 and MN6 ($V_{GS} \leq $Vth). Also, a drain-source voltage $V_{DS}$ of each of the fifth and sixth NMOS transistors MN5 and MN6 is biased to be higher than 0 V ($V_{DS}>0$). Accordingly, each of the fifth and sixth NMOS transistors MN5 and MN6 may perform a sub-threshold operation.

The amplifier 230 may include second through fourth PMOS transistors MP2 through MP4, seventh and eighth NMOS transistors MN7 and MN8, and a resistor R.

The second PMOS transistor MP2 may include a source, to which the power voltage VDD is connected, a gate, to which the gate and the drain of the third PMOS transistor MP3 are connected, and a drain, to which a fifth node NA5 is connected. The third PMOS transistor MP3 may include a source, to which the power voltage VDD is connected, and a gate and a drain, which are connected to each other. The second and third PMOS transistors MP2 and MP3 may form a current mirror structure. The fourth PMOS transistor MP4 may include a source, to which the power voltage VDD is connected, a gate, to which the fifth node NA5 is connected, and a drain, to which the resistor R is connected. A connection node between the fourth PMOS transistor MP4 and the resistor R may be an output node OUT of the reference voltage circuit 126 and may output the reference voltage $V_{REF}$.

The seventh NMOS transistor MN7 may include a drain, to which the gate and the drain of the third PMOS transistor MP3 are connected, a gate, to which the third node NP3 is connected, and a source, to which a drain of the eight NMOS transistor MN8 is connected. The eighth NMOS transistor MN8 may include the drain, to which the source of the seventh NMOS transistor MN7 is connected, a gate, to which the output node OUT is connected, and a source, to which the ground voltage VSS is connected.

The voltage $V_{PTAT2}$ of the third node NP3, which is output from the second current bias circuit 220, is connected to the gate of the seventh NMOS transistor MN7 in the amplifier 230, wherein the seventh NMOS transistor MN7 may be symmetrical to the fifth NMOS transistor MN5 of the second current bias circuit 220, the fifth NMOS transistor MN5 including the gate, to which the voltage $V_{PTAT2}$ of the third node NP3 is connected.

When aspect ratios W/L, ratios of widths to lengths, of the second and third PMOS transistors MP2 and MP3 forming the current mirror structure are set to be the same, the same current may flow in the second and third PMOS transistors MP2 and MP3. A current of the seventh NMOS transistor MN7 may be the same as a current of the fifth NMOS transistor MN5. Also, a current that is the same as a current of the sixth NMOS transistor connected in series with the fifth NMOS transistor MN5 may flow in the eighth NMOS transistor MN8 connected in series with the seventh NMOS transistor MN7. Accordingly, a voltage that is the same as the voltage $V_{PTAT3}$ of the fourth node NP4 may be developed to the output node OUT connected to the gate of the eighth NMOS transistor MN8, and may be output as the reference voltage $V_{REF}$.

Figure 4:
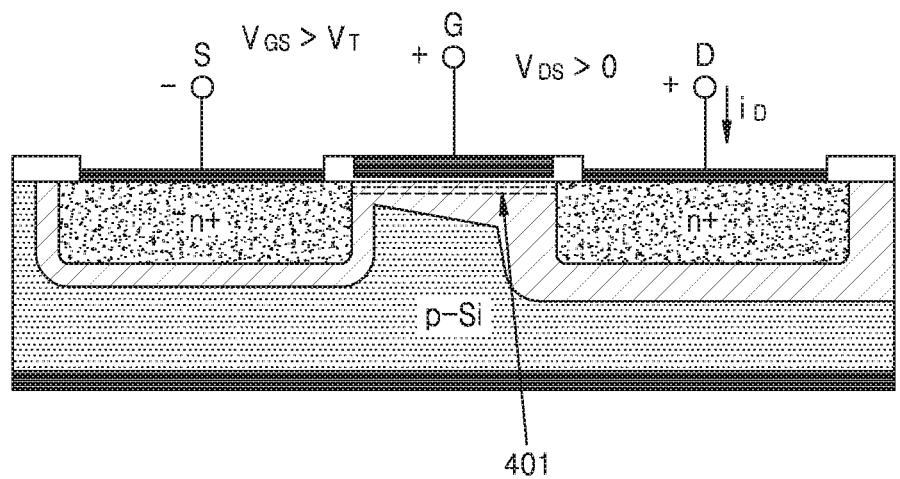
FIGS. 4 through 8 are diagrams for describing a general N-channel metal oxide semiconductor (NMOS) transistor according to various example embodiments.
Figure 5:
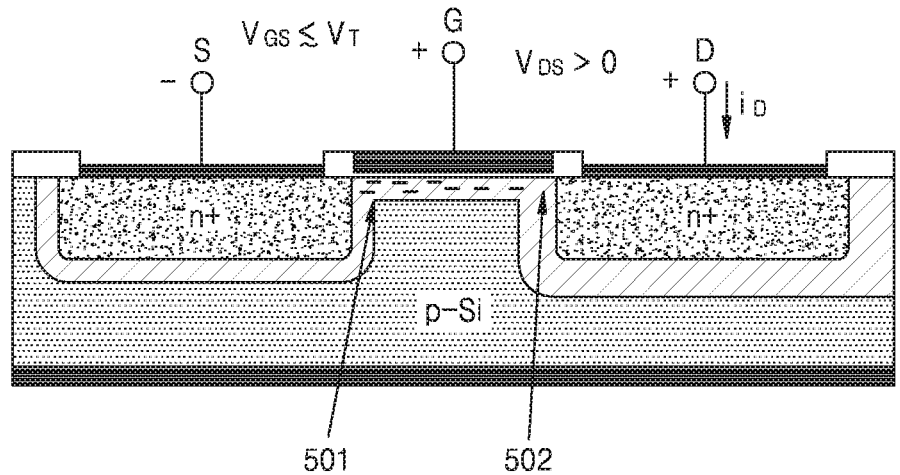
Figure 6:
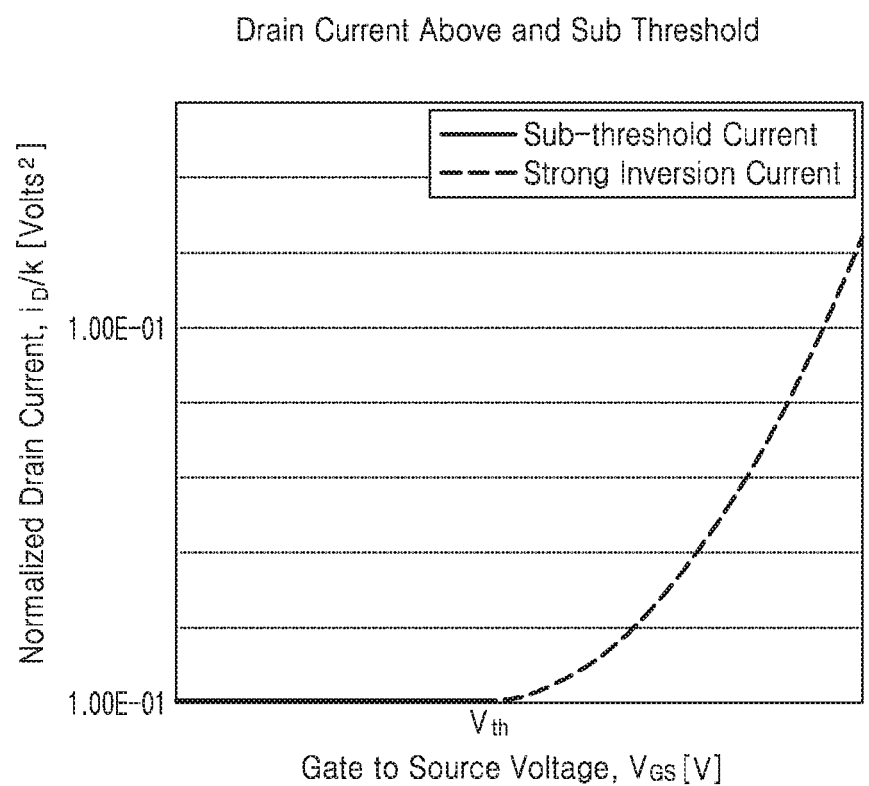
Figure 7:
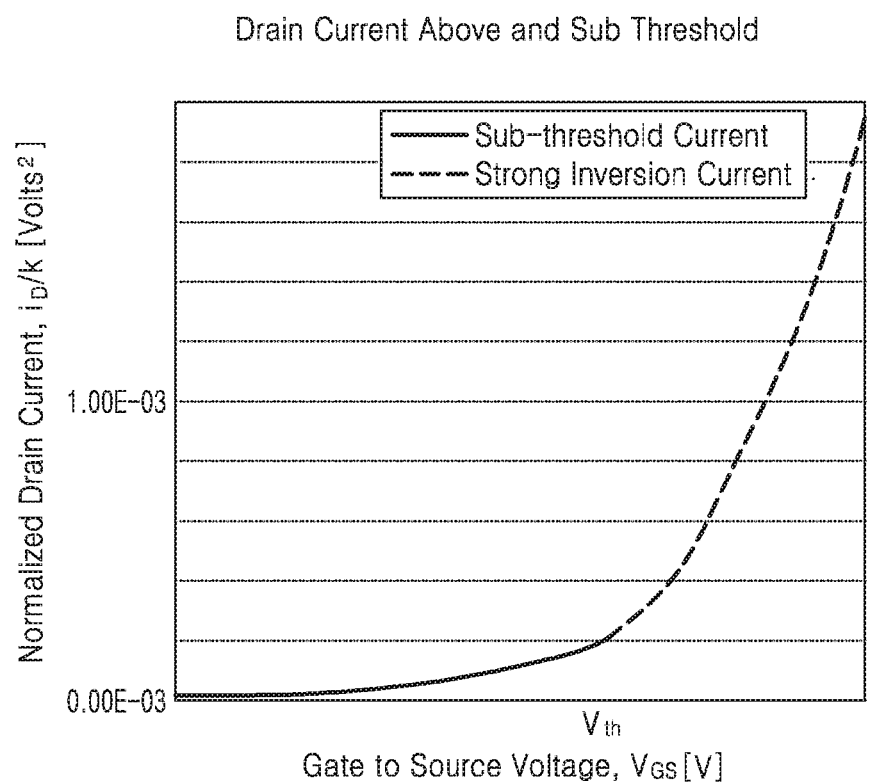
Figure 8:
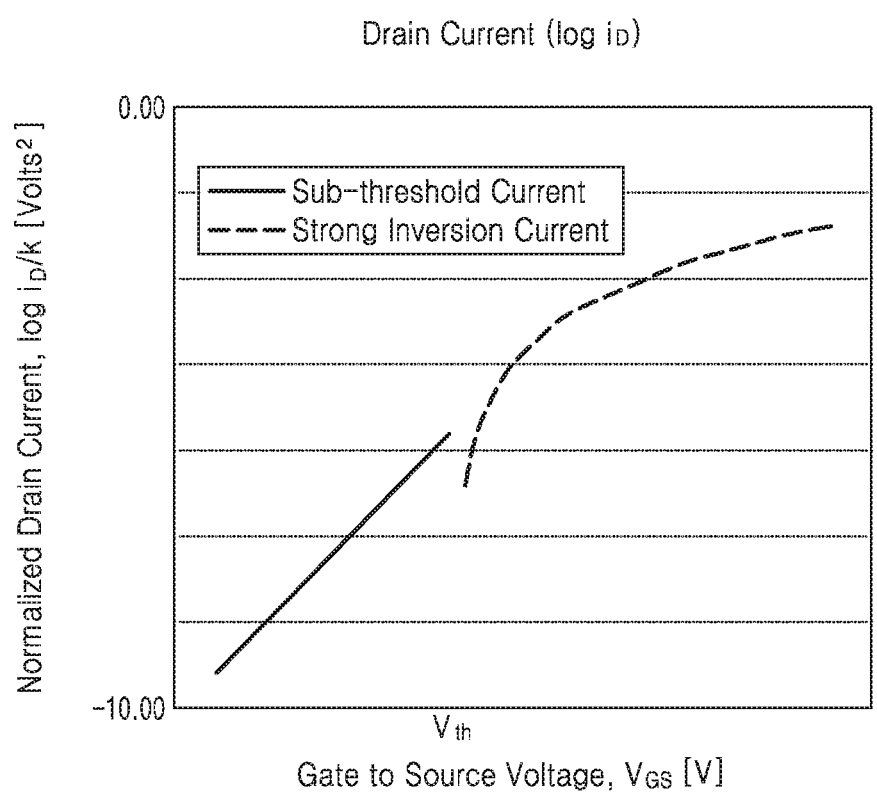

FIGS. 4 through 8 are diagrams for describing a general NMOS transistor according to various example embodiments. FIG. 4 is a diagram for describing a general strong inversion operation from among operation models of the NMOS transistors. FIG. 5 is a diagram for describing a sub-threshold operation of the NMOS transistors. FIGS. 6 through 8 are graphs for describing the sub-threshold operation. In FIGS. 6 through 8, a horizontal axis indicates a gate-source voltage $V_{Gs}$ of the NMOS transistor and a vertical axis indicates a drain current $i_D$.

Referring to FIG. 4, when the gate-source voltage $V_{Gs}$ between a gate G and a source S of the NMOS transistor is greater than a threshold voltage Vth of the NMOS transistor, and a drain-source voltage $V_{DS}$ ($V_{DS}>0$) is applied between a drain D and the source S of the NMOS transistor, a strong inversion layer is formed on a substrate surface p-Si below the gate G to induce a high-conductive n-type channel 401. Highly-concentrated electrons in the strong inversion layer are drifted from the source S to the drain D, due to an electrical field formed by the drain-source voltage $V_{DS}$ between the drain D and the source S. Accordingly, a strong inversion drain current $i_D$ may flow from the drain D to the source S.

Referring to FIG. 5, when the gate-source voltage $V_{Gs}$ between the gate G and the source S of the NMOS transistor is equal to or less than the threshold voltage Vth of the NMOS transistor, the high-conductive n-type channel 401 is not formed in the substrate surface p-Si below the gate G. A diffusion flux is formed from the source S to the drain D by the drain-source voltage $V_{DS}$ ($V_{DS}>0$) between the drain D and the source S, and thus, a few number of electrons 501 in the source S may overcome a barrier and may be diffused to the drain D. In this case, the electrons are not affected by the drain-source voltage $V_{DS}$ until the electrons reach an edge of a depletion area 502. Accordingly, a sub-threshold drain current $i_D$ of a very small magnitude flows from the drain D to the source S.

Referring to FIG. 6, the drain current $i_D$, which flows until the gate-source voltage $V_{GS}$ between the gate G and the source S reaches the threshold voltage Vth of the NMOS transistor, corresponds to the sub-threshold drain current $i_D$, which is almost zero, as described in FIG. 5. When the gate-source voltage $V_{GS}$ is greater than the threshold voltage Vth, the drain current $I_D$ corresponds to the strong inversion drain current $I_D$ which has a large magnitude and quickly flows, as described in FIG. 4.

Referring to FIG. 7, the gate-source voltage $V_{GS}$ of FIG. 6 has magnified the drain current $i_D$ approximate to the threshold voltage Vth by 100 times. FIG. 7 shows a flow of the sub-threshold drain current $I_D$ of a very small magnitude, rather than the sub-threshold drain current $I_D$ equal to 0.

Referring to FIG. 8, the drain current $i_D$ of FIG. 7 is altered according to a log scale. FIG. 8 shows that the sub-threshold drain current $I_D$ has linearity having a predetermined gradient.

The sub-threshold drain current $i_D$ of the NMOS transistor, described in FIGS. 4 through 8, may be represented via Equation 3.

$$i_{D(subthreshold)} = \frac{W}{L}\mu_n C_{ox}(m-1)\, V_T^2\, e^{(V_{GS}-V_{th})/m\, V_T}\left(1 - e^{-q\, V_{DE}/kT}\right) \quad \text{[Equation 3]}$$

Here, W and L denote a width and a length of a channel of the NMOS transistor, respectively, $\mu_n$ denotes an electron mobility, $C_{ox}$ denotes a gate capacitance, m denotes a sub-threshold gradient (=(1+Cd/Cox)), Cd denotes a drain capacitance, $V_T$ denotes a thermal voltage (=kT/q), q denotes a charge of an electron, k denotes Boltzmann's constant, and T denotes an operation temperature in the Kelvin temperature scale.

In Equation 3, $(1-e^{-qV_{DS}/kT})$ is almost 1 due to the drain-source voltage $V_{DS}$ of the NMOS transistor. That is, $(1-e^{-qV_{DS}/kT}) \approx 1$ may be used. Accordingly, the sub-threshold drain current $i_D$ of the NMOS transistor may be represented by Equation 4.

$$i_{D(subthreshold)} = \frac{W}{L}\mu_n C_{ox}(m-1)\, V_T^2\, e^{(V_{GS}-V_{th})/m\, V_T} \quad \text{[Equation 4]}$$

Figure 9:
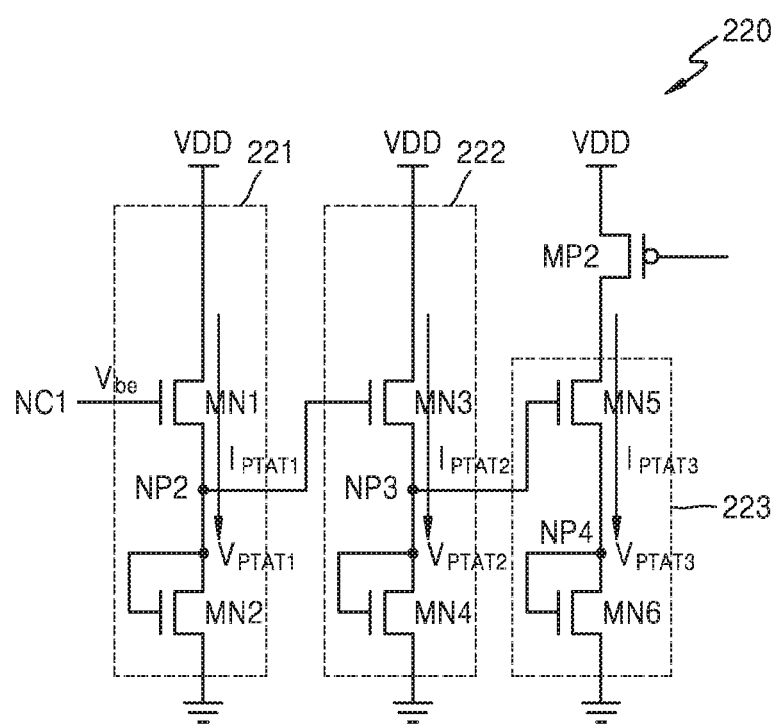
FIG. 9 is a diagram for describing an operation of a second current bias circuit of FIG. 2 according to an example embodiment.

FIG. 9 is a diagram for describing a detailed operation of the second current bias circuit 220 of FIG. 2.

Referring to FIG. 9, each of the first and second NMOS transistors MN1 and MN2 of the first sub-threshold operation circuit 221 in the second current bias circuit 220 may, based on the sub-threshold operation of each of the first and second NMOS transistors MN1 and MN2, allow the sub-threshold drain current $i_D$ of the NMOS transistor described with reference to FIGS. 4 through 8 to flow.

A drain current $i_{PTAT1}$ of the first NMOS transistor MN1 may be obtained based on Equation 5 by substituting a width W1 and a length L1 of a channel of the first NMOS transistor MN1 and the gate-source voltage $V_{GS}$ ($=V_{be}-V_{PTAT1}$) in Equation 4.

$$i_{PTAT1} = \frac{W1}{L1}\mu_n\, C_{ox}(m-1)\, V_T^2\, e^{(V_{be}-V_{PTAT1}-V_{th})/m\, V_T} \quad \text{[Equation 5]}$$

The drain current $i_{PTAT1}$ of the first NMOS transistor MN1 is the same as a drain current $i_{PTAT1}$ of the second NMOS transistor MN2 connected in series with the first NMOS transistor MN1. The drain current $i_{PTAT1}$ of the second NMOS transistor MN2 may be obtained based on Equation 6 by substituting a width W2 and a length L2 of a channel of the second NMOS transistor MN2 and the gate-source voltage $V_{Gs}$ ($=V_{PTAT1}$) in Equation 4. The voltage $V_{PTAT1}$ is the voltage of the second node NP2.

$$i_{PTAT1} = \frac{W2}{L2}\mu_n\, C_{ox}(m-1)\, V_T^2\, e^{(V_{PTAT1}-V_{th})/m\, V_T} \quad \text{[Equation 6]}$$

Equation 7 may be obtained from Equation 5 and Equation 6.

$$\frac{W1}{L1}\mu_n\, C_{ox}(m-1)\, V_T^2\, e^{(V_{be}-V_{PTAT1}-V_{th})/m\, V_T} = \\ \frac{W2}{L2}\mu_n\, C_{ox}(m-1)\, V_T^2\, e^{(V_{PTAT1}-V_{th})/m\, V_T} \quad \text{[Equation 7]}$$

When the voltage $V_{PTAT1}$ of the second node NP2 is calculated via Equation 7, Equation 8 is obtained.

$$V_{PTAT1} = \frac{1}{2}V_{be} + \frac{1}{2}m\, V_T \ln\!\left(\frac{W1L2}{L1W2}\right) \quad \text{[Equation 8]}$$

It is to be understood that the voltage $V_{PTAT1}$ of the second node NP2 depends on the widths W1 and W2 and the lengths L1 and L2 of the channels of the first and second NMOS transistors MN1 and MN2.

The first NMOS transistor MN1 performs the sub-threshold operation whereby the gate-source voltage $V_{GS}$ is lower than the threshold voltage Vth of the first NMOS transistor MN1. Thus, the voltage $V_{PTAT1}$ of the second node NP2, which is the source of the first NMOS transistor MN1, may be lower than the voltage $V_{be}$ of the first node NC1, which is the gate of the first NMOS transistor MN1, and a difference between the voltage $V_{be}$ of the first node NC1 and the voltage $V_{PTAT1}$ of the second node NP2 may be less than the threshold voltage Vth of the first NMOS transistor MN1. The voltage $V_{PTAT1}$ of the second node NP2 may be provided to the second sub-threshold operation circuit 222.

The second sub-threshold operation circuit 222 may include the third and fourth NMOS transistors MN3 and MN4 connected in series between the power voltage VDD and the ground voltage VSS. The third NMOS transistor MN3 may include a drain, to which the power voltage VDD is connected, a gate, to which the second node NP2 is connected, and a source, to which the third node NP3 is connected. The fourth NMOS transistor MN4 may include a gate and a drain, to which the third node NP3 is connected, and a source, to which the ground voltage VSS is connected.

The voltage $V_{PTAT1}$ of the second node NP2 is applied to the gate of the third NMOS transistor MN3. The voltage $V_{PTAT1}$ of the second node NP2 is lower than the voltage $V_{be}$ of the first node NC1 inducing the sub-threshold operations of the first and second NMOS transistors MN1 and MN2. Thus, the third and fourth NMOS transistors MN3 and MN4 having the same connection structure as the first and second NMOS transistors MN1 and MN2 may each perform a sub-threshold operation.

A drain current $i_{PTAT2}$ of the third NMOS transistor MN3 may be obtained based on Equation 9, by substituting a width W3 and a length L3 of a channel of the third NMOS transistor MN3 and the gate-source voltage $V_{GS}$ (=$V_{PTAT1}$−$V_{PTAT2}$) in Equation 4.

$$i_{PTAT2} = \frac{W3}{L3} \mu_n \, C_{ox}(m-1) \, V_T^2 \, e^{(V_{PTAT1}-V_{PTAT2}-V_{th})/m V_T} \quad \text{[Equation 9]}$$

The drain current $i_{PTAT2}$ of the third NMOS transistor MN3 is the same as a drain current $i_{PTAT2}$ of the fourth NMOS transistor MN4 connected in series with the third NMOS transistor MN3. The drain current $i_{PTAT2}$ of the fourth NMOS transistor MN4 may be obtained as shown in Equation 10, by substituting a width W4 and a length L4 of a channel of the fourth NMOS transistor MN4 and the gate-source voltage VGS (=$V_{PTAT2}$) to Equation 4. The voltage $V_{PTAT2}$ is a voltage of the third node NP3.

$$i_{PTAT2} = \frac{W4}{L4} \mu_n \, C_{ox}(m-1) \, V_T^2 \, e^{(V_{PTAT1}-V_{th})/m V_T} \quad \text{[Equation 10]}$$

Equation 11 may be obtained from Equation 9 and Equation 10.

$$\frac{W3}{L3} \mu_n \, C_{ox}(m-1) \, V_T^2 \, e^{(V_{PTAT1}-V_{PTAT2}-V_{th})/m V_T} = \quad \text{[Equation 11]}$$
$$\frac{W4}{L4} \mu_n \, C_{ox}(m-1) \, V_T^2 \, e^{(V_{PTAT1}-V_{th})/m V_T}$$

Equation 12 may be obtained by calculating the voltage $V_{PTAT2}$ of the third node NP3 by substituting the voltage $V_{PTAT1}$ of Equation 8 in Equation 11.

$$V_{PTAT2} = \frac{1}{4} V_{be} + \frac{1}{4} m \, V_T \ln\left(\frac{W1 L2}{L1 W2} \frac{W3 L4}{L3 W4}\right) \quad \text{[Equation 12]}$$

It is to be understood that the voltage $V_{PTAT2}$ of the third node NP3 depends on the widths W1 and W2 and the lengths L1 and L2 of the channels of the first and second NMOS transistors MN1 and MN2, and the widths W3 and W4 and the lengths L3 and L4 of the channels of the third and fourth NMOS transistors MN3 and MN4.

The third NMOS transistor MN3 performs the sub-threshold operation whereby the gate-source voltage $V_{GS}$ is lower than the threshold voltage Vth of the third NMOS transistor MN3. Thus, the voltage $V_{PTAT2}$ of the third node NP3, which is the source of the third NMOS transistor MN3, may be lower than the voltage $V_{PTAT1}$ of the second node NP2, which is the gate of the third NMOS transistor MN3, and a difference between the voltage $V_{PTAT1}$ of the second node NP2 and the voltage $V_{PTAT2}$ of the third node NP3 may be less than the threshold voltage Vth of the third NMOS transistor MN3. The voltage $V_{PTAT2}$ of the third node NP3 may be provided to the third sub-threshold operation circuit 223.

The third sub-threshold operation circuit 223 may include the fifth and sixth NMOS transistors MN5 and MN6 connected in series with each other. The fifth NMOS transistor MN5 may include a drain, to which the fifth node NA5 of the amplifier 230 is connected, a gate, to which the third node NP3 is connected, and a source, to which the fourth node NP4 is connected. The sixth NMOS transistor MN6 may include a gate and a drain, to which the fourth node NP4 is connected, and a source, to which the ground voltage VSS is connected.

The voltage $V_{PTAT2}$ of the third node NP3 is applied to the gate of the fifth NMOS transistor MN5. The voltage $V_{PTAT2}$ of the third node NP3 is lower than the voltage $V_{PTAT1}$ of the second node NP2 inducing the sub-threshold operations of the third and fourth NMOS transistors MN3 and MN4 of the second sub-threshold operation circuit 222. Thus, the fifth and sixth NMOS transistors MN5 and MN6 having the same connection structure as the third and fourth NMOS transistors MN3 and MN4 may each perform a sub-threshold operation.

A drain current $i_{PTAT3}$ of the fifth NMOS transistor MN5 may be based on in Equation 13 by substituting a width W5 and a length L5 of a channel of the fifth NMOS transistor MN5 and the gate-source voltage $V_{GS}$ (=$V_{PTAT2}$−$V_{PTAT3}$) in Equation 4.

$$i_{PTAT3} = \frac{W5}{L5} \mu_n \, C_{ox}(m-1) \, V_T^2 \, e^{(V_{PTAT2}-V_{PTAT3}-V_{th})/m V_T} \quad \text{[Equation 13]}$$

The drain current $i_{PTAT3}$ of the fifth NMOS transistor MN5 is the same as a drain current $i_{PTAT3}$ of the sixth NMOS transistor MN6 connected in series with the fifth NMOS transistor MN5. The drain current $i_{PTAT3}$ of the sixth NMOS transistor MN6 may be obtained based on Equation 14 by substituting a width W6 and a length L6 of a channel of the sixth NMOS transistor MN6 and the gate-source voltage $V_{Gs}$ (=$V_{PTAT3}$) in Equation 4. The voltage $V_{PTAT3}$ is a voltage of the fourth node NP4.

$$i_{PTAT3} = \frac{W6}{L6} \mu_n \, C_{ox}(m-1) \, V_T^2 \, e^{(V_{PTAT3}-V_{th})/m V_T} \quad \text{[Equation 14]}$$

Equation 15 may be obtained from Equation 13 and Equation 14.

$$\frac{W5}{L5}\mu_n C_{ox}(m-1) V_T^2 e^{(V_{PTAT2}-V_{PTAT3}-V_{th})/m V_T} = \qquad \text{[Equation 15]}$$
$$\frac{W6}{L6}\mu_n C_{ox}(m-1) V_T^2 e^{(V_{PTAT3}-V_{th})/m V_T}$$

Equation 16 may be obtained by calculating the voltage $V_{PTAT3}$ of the fourth node NP4 by substituting the voltage $V_{PTAT2}$ of Equation 12 in Equation 15.

$$V_{PTAT3} = \frac{1}{8}V_{be} + \frac{1}{8}m\ V_T\ln\left(\frac{W1L2}{L1W2}\left(\frac{W3L4}{L3W4}\right)^2\left(\frac{W5L6}{L5W6}\right)^4\right) \qquad \text{[Equation 16]}$$

It is to be understood that the voltage $V_{PTAT3}$ of the fourth node NP4 depends on the widths W1 and W2 and the lengths L1 and L2 of the channels of the first and second NMOS transistors MN1 and MN2, the widths W3 and W4 and the lengths L3 and L4 of the channels of the third and fourth NMOS transistors MN3 and MN4, and the widths W5 and W6 and the lengths L5 and L6 of the channels of the fifth and sixth NMOS transistors MN5 and MN6.

Figure 16:
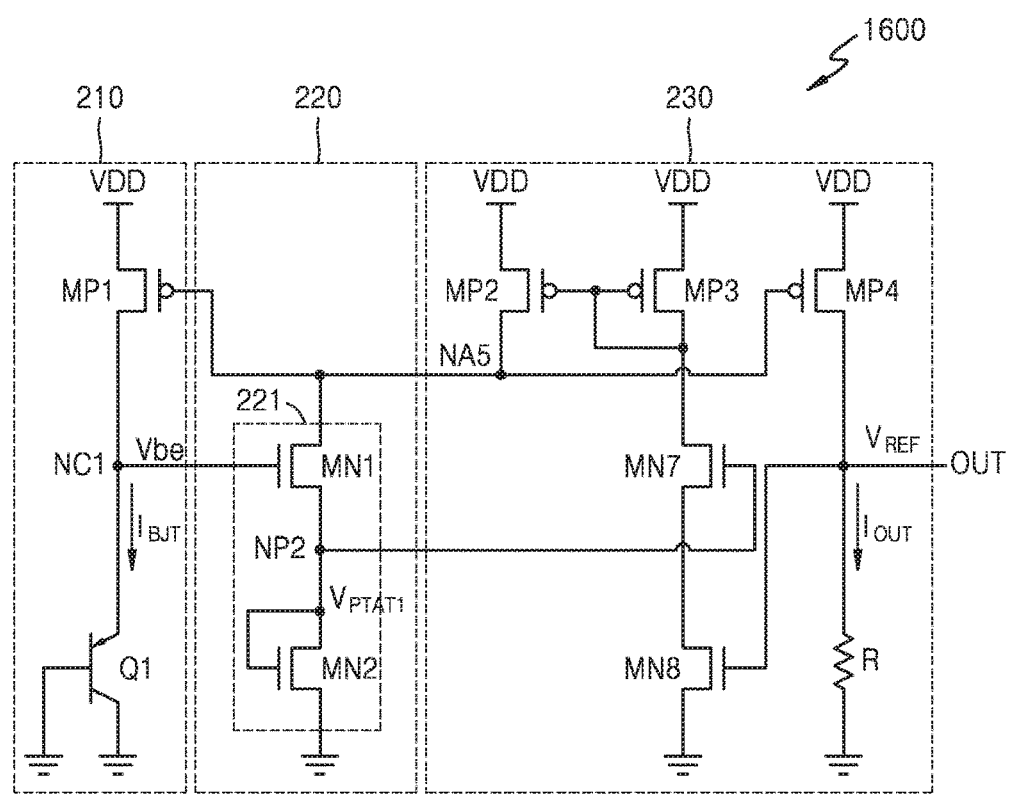

The voltage $V_{PTAT1}$ of the second node NP2 of Equation 8, the voltage $V_{PTAT2}$ of the third node NP3 of Equation 12, and the voltage $V_{PTAT3}$ of the fourth node P4 of Equation 16 are respectively correlated with the widths W1 and W2 and the lengths L1 and L2 of the channels of the first and second NMOS transistors MN1 and MN2, the widths W3 and W4 and the lengths L3 and L4 of the channels of the third and fourth NMOS transistors MN3 and MN4, and the widths W5 and W6 and the lengths L5 and L6 of the channels of the fifth and sixth NMOS transistors MN5 and MN6, wherein Equations 8, 12, and 16 may function as referential factors for determining a chip area of the reference voltage circuit 126 to be described with reference to FIGS. 15 and 16.

Figure 10:
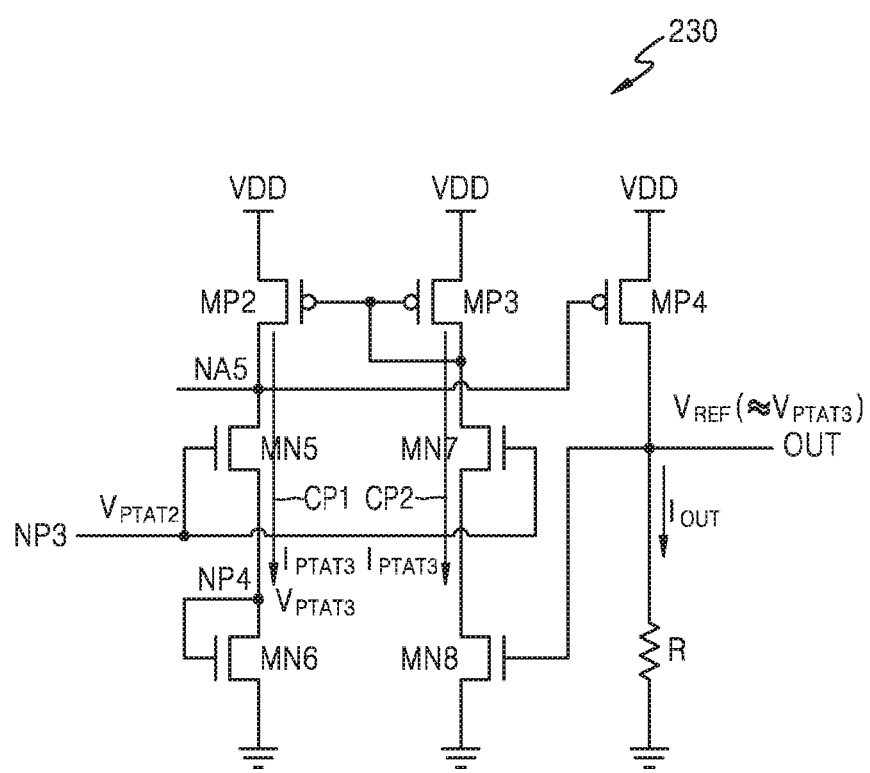
FIG. 10 is a diagram for describing an operation of an amplifier of FIG. 2 according to an example embodiment.

FIG. 10 is a diagram for describing an operation of the amplifier 230 of FIG. 2.

Referring to FIG. 10, the amplifier 230 may operate in connection with the third sub-threshold operation circuit 223 described in FIG. 9. It is assumed that the second and third PMOS transistors MP2 and MP3 have the same aspect ratios W/L, that is, ratios of widths to lengths, so that the same current flows in the second and third PMOS transistors MP2 and MP3 forming the current mirror structure. Also, it is assumed that the fifth and seventh NMOS transistors MN5 and MN7 have the same aspect ratios W/L and the sixth and eighth NMOS transistors MN6 and MN8 have the same aspect ratios W/L.

The same current flows in the second and third PMOS transistors MP2 and MP3, and the seventh NMOS transistor MN7 including the gate, to which the voltage $V_{PTAT2}$ of the third node NP3 is connected, and the fifth NMOS transistor MN5 including the gate, to which the voltage $V_{PTAT2}$ of the third node NP3 is connected, are symmetrical to each other. A current of the seventh NMOS transistor MN7 connected in series with the third PMOS transistor MP3 may be the same as the current $I_{PTAT3}$ of the fifth NMOS transistor MN5 connected in series with the second PMOS transistor MP2. Also, a current that is the same as the current $I_{PTAT3}$ of the sixth NMOS transistor MN6 connected in series with the fifth NMOS transistor MN5 may flow in the eighth NMOS transistor MN8 connected in series with the seventh NMOS transistor MN7.

A path CP1 of the current $I_{PTAT3}$ flowing in the second PMOS transistor MP2 and the fifth and sixth NMOS transistors MN5 and MN6 and a path CP2 of the current $I_{PTAT3}$ flowing in the third PMOS transistor MP3 and the seventh and eighth NMOS transistors MN7 and MN8 may have the same structure. Thus, a voltage having the same value as a voltage of the gate of the sixth NMOS transistor may be developed in the gate of the eighth NMOS transistor MN8. The output node OUT connected to the gate of the eighth NMOS transistor MN8 may have a voltage having the same value as the voltage $V_{PTAT3}$ of the forth node NP4, which is the voltage of the gate of the sixth NMOS transistor MN6, and the voltage may be output as the reference voltage $V_{REF}$.

That the output node OUT of the amplifier 230 outputs the voltage $V_{PTAT3}$ of the fourth node NP4 of the second current bias circuit 220 connected to a front end of the amplifier 230 denotes that a gain of the amplifier 230 is 1. The voltage $V_{PTAT3}$ of the fourth node NP4 may have a very low value that is determined based on the sub-threshold operation of the sixth NMOS transistor MN6. The voltage $V_{PTAT3}$ of the fourth node NP4 is lower than the voltages $V_{be}$, $V_{PTAT1}$, and $V_{PTAT2}$ of the first through third nodes NC1, NP2, and NP3, which allow the NMOS transistors MN1 through MN6 of the first through third sub-threshold operation circuits 221 through 223 in the second current bias circuit 220 (FIG. 9) to perform the sub-threshold operations. Thus, the amplifier 230 may output the reference voltage $V_{REF}$ having a very low value.

The output current $I_{out}$ flowing in the resistor R by the reference voltage $V_{REF}$ of the output node OUT of the amplifier 230 corresponds to Equation 17.

$$I_{OUT} = V_{REF}/R \qquad \text{[Equation 17]}$$

The output current $I_{out}$ flowing in the output node OUT of the amplifier 230 may be the same as a current flowing in the fourth PMOS transistor MP4 connected in series with the resistor R. That is, the output current $I_{out}$ may flow in the fourth PMOS transistor MP4.

Figure 11:
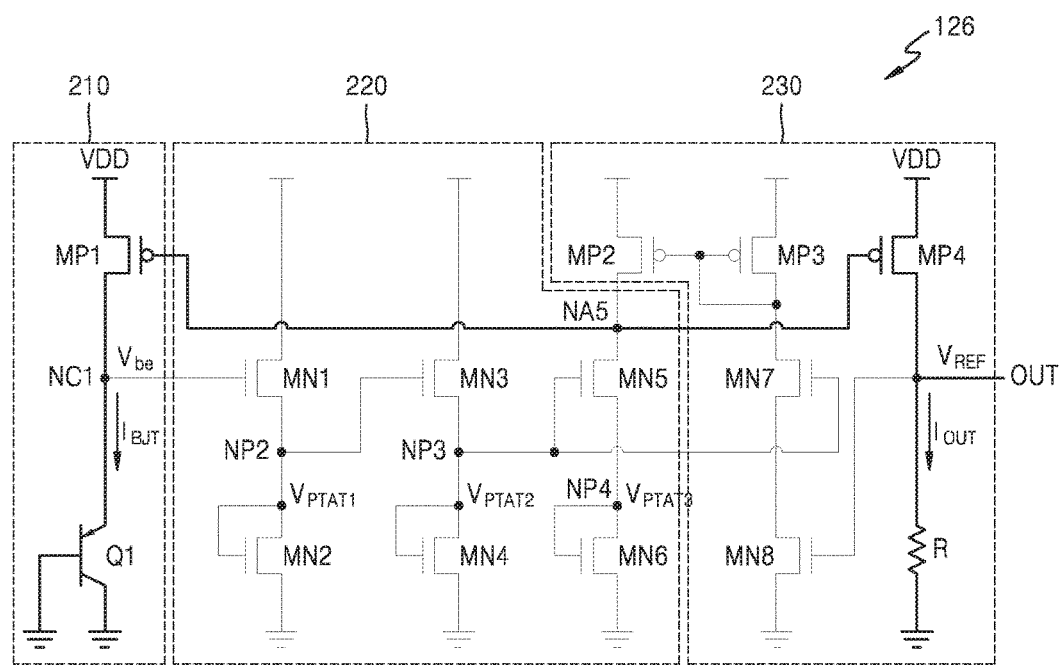
FIG. 11 is a diagram for describing operations of a first current bias circuit and the amplifier of FIG. 2 according to an example embodiment.

FIG. 11 is a diagram for describing operations of the first current bias circuit 210 and the amplifier 230 of FIG. 2.

Referring to FIG. 11, the output current $I_{out}$ flowing in the fourth PMOS transistor MP4 of the amplifier 230 may induce the first current $I_{bjt}$ of the first current bias circuit 210. The fourth PMOS transistor MP4 may include the source, to which the power voltage VDD is connected, the gate, to which the fifth node NA5 is connected, and the drain, to which the output node OUT is connected. The first PMOS transistor MP1 of the first current bias circuit 210 may include the source, to which the power voltage VDD is connected, the gate, to which the fifth node NA5 is connected, and the drain, to which the emitter of the PNP bipolar transistor Q1 is connected.

The power voltage VDD is commonly connected to the sources of the first and fourth PMOS transistors MP1 and MP4, and the fifth node NA is commonly connected to the gates of the first and fourth PMOS transistors MP1 and MP4, and thus, the gate-source voltages $V_{GS}$ of the first and fourth PMOS transistors MP1 and MP4 may be the same. Accordingly, the output current $I_{out}$ of the fourth PMOS transistor MP4 may be the same as the current of the first PMOS transistor MP1. That is, the first current $I_{bjt}$ of the first current bias circuit 210, corresponding to the output current $I_{out}$ of the amplifier 230, may be induced.

As described above, the reference voltage circuit 126 may use the NMOS transistors MN1 through MN8 performing the sub-threshold operations, and may generate the reference voltage $V_{REF}$ based on the sub-threshold drain currents of the NMOS transistors MN1 through MN8. Accordingly, the reference voltage circuit 126 consumes a power equal to or less than hundreds of nW, and the reference voltage circuit 126 may be used in the terminal device 120 having ultra-low power consumption.

Figure 12:
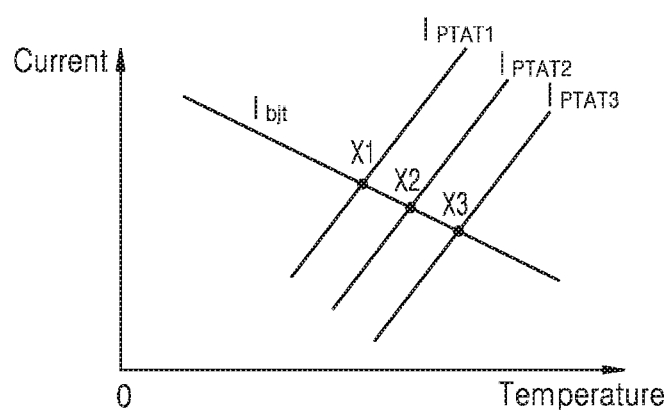
FIGS. 12 and 13 are graphs for describing a temperature characteristic of the reference voltage circuit of FIG. 2 according to various example embodiments.
Figure 13:
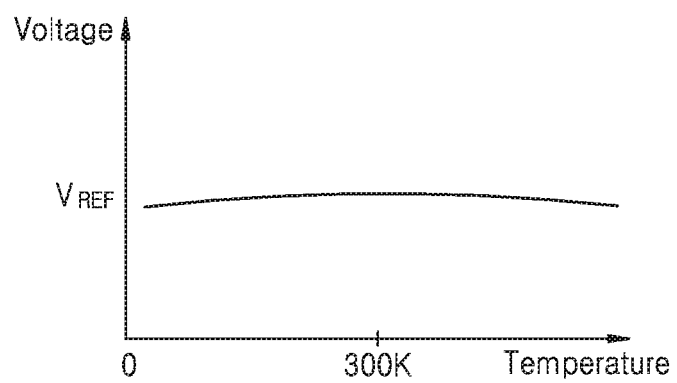

FIGS. 12 and 13 are graphs for describing a temperature characteristic of the reference voltage circuit 126 of FIG. 2. A horizontal axis of FIG. 12 denotes Kelvin temperature, and a vertical axis denotes a current. A horizontal axis of FIG. 13 denotes Kelvin temperature and a vertical axis denotes a voltage.

Referring to FIG. 12, the first current $I_{bjt}$ of the first current bias circuit 210 may have a CTAT current characteristic that is inversely proportional to absolute temperature. The current $I_{PTAT1}$ of the first sub-threshold operation circuit 221 of the second current bias circuit 220 has a proportional to absolute temperature (PTAT) characteristic that is proportional to absolute temperature. The current $I_{PTAT2}$ of the second sub-threshold operation circuit 222 is less than the current $I_{PTAT1}$ of the first sub-threshold operation circuit 221, and the current $I_{PTAT}3$ of the third sub-threshold operation circuit 223 is less than the current $I_{PTAT2}$ of the second sub-threshold operation circuit 222.

A point X1, at which the first current $I_{bjt}$ of the first current bias circuit 210 meets the current $I_{PTAT1}$ of the first sub-threshold operation circuit 221, a point X2, at which the first current $I_{bjt}$ of the first current bias circuit 210 meets the current $I_{PTAT2}$ of the second sub-threshold operation circuit 222, and a point X3, at which the first current $I_{bjt}$ of the first current bias circuit 210 meets the current $I_{PTAT3}$ of the third sub-threshold operation circuit 223 may be found. Positions of the points X1, X2, and X3 in the graph are lowered in this stated order, so that the reference voltage $V_{REF}$ of the reference voltage circuit 126 (FIG. 2) may be determined at the point X3, at which the CTAT characteristic graph of the first current $I_{bjt}$ of the first current bias circuit 210 and the PTAT characteristic graph of the current $I_{PTAT3}$ of the third sub-threshold operation circuit 223 meet. Accordingly, the reference voltage circuit 126 may generate the reference voltage $V_{REF}$ at room temperature of about 300 K, irrespective of a temperature change, as illustrated in FIG. 13. That is, the reference voltage circuit 126 may generate the reference voltage $V_{REF}$ having low temperature dependence.

Figure 14:
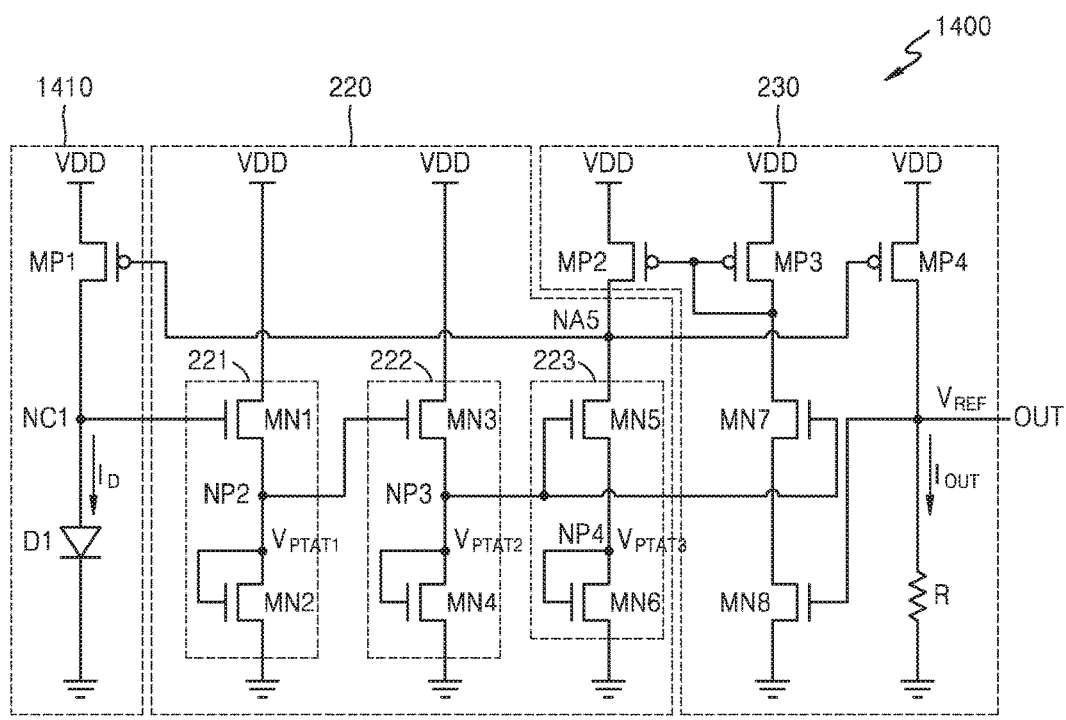
FIGS. 14 through 16 are circuit diagrams of a reference voltage circuit according to various example embodiments.

FIGS. 14 through 16 are respectively circuit diagrams for describing reference voltage circuits 1400, 1500, and 1600 according to example embodiments. The reference voltage circuits 1400, 1500, and 1600 of FIGS. 14 through 16, respectively, correspond to the reference voltage circuit 126 included in the terminal device 120 of FIG. 1. For convenience, differences from the reference voltage circuit 126 of FIG. 2 will be mainly described below.

The reference voltage circuit 1400 of FIG. 14 differs from the reference voltage circuit 126 of FIG. 2 in that the reference voltage circuit 1400 includes a diode D1 in a first current bias circuit 1410. The diode D1 may include an anode, to which the first node NC1 is connected, and a cathode, to which the ground voltage VSS is connected. A diode voltage $V_D$ of the first node NC1 may be expressed by Equation 18.

$$V_D = V_T \ln\left(\frac{I_D}{I_S}\right) \quad \text{[Equation 18]}$$

According to Equation 18, a temperature voltage $V_T$ increases as a temperature increases, but a saturation current $I_S$ increases by a much greater percentage than the temperature voltage $V_T$, and thus, the diode voltage $V_D$ has a CTAT voltage characteristic. The diode voltage $V_D$ may be a voltage of the first node NC1 and may be provided to the second current bias circuit 220. A diode current $I_D$ flowing in the first node NC1 may be a first current, which is the same as the drain current of the first PMOS transistor MP1, and may have the same value as the output current $I_{out}$ of the amplifier 230.

The reference voltage circuit 1500 of FIG. 15 does not include the second sub-threshold operation circuit 222 in the second current bias circuit 220, unlike the reference voltage circuit 126 of FIG. 2. The second node NP2 of the first sub-threshold operation circuit 221 may be connected to the gates of the fifth NMOS transistor MN5 of the third sub-threshold operation circuit 223 and the seventh NMOS transistor MN7 of the amplifier 230.

The reference voltage circuit 1500 may determine the reference voltage $V_{REF}$ at the point X2 illustrated in FIG. 12, at which the CTAT characteristic graph of the first current $I_{bjt}$ of the first current bias circuit 210 meets the PTAT characteristic graph of the current $I_{PTAT2}$ of the second sub-threshold operation circuit 222. The reference voltage $V_{REF}$ generated by the reference voltage circuit 1500 may correspond to the voltage $V_{PTAT2}$ of the third node NP3 described in FIG. 9.

The reference voltage circuit 1600 of FIG. 16 does not include the second and third sub-threshold operation circuits 222 and 223 in the second current bias circuit 220, unlike the reference voltage circuit 126 of FIG. 2. The second node NP2 of the first sub-threshold operation circuit 221 may be connected to the gate of the seventh NMOS transistor MN7 of the amplifier 230, and the drain of the second PMOS transistor MP2 of the amplifier 230 may be connected to the drain of the first NMOS transistor MN1.

The reference voltage circuit 1600 may determine the reference voltage $V_{REF}$ at the point X1 illustrated in FIG. 12, at which the CTAT characteristic graph of the first current $I_{bjt}$ of the first current bias circuit 210 meets the PTAT characteristic graph of the current $I_{PTAT1}$ of the first sub-threshold operation circuit 221. The reference voltage $V_{REF}$ generated by the reference voltage circuit 1600 may correspond to the voltage $V_{PTAT1}$ of the second node NP2 described in FIG. 9.

The reference voltage circuits 126, 1500, and 1600 of FIGS. 2, 15, and 16, respectively, are correlated with chip areas of the reference voltage circuits in an integrated circuit, in connection with Equations 8, 12, and 16 described above.

The voltage $V_{PTAT1}$ of the second node NP2 of Equation 8 depends on the widths W1 and W2 and the lengths L1 and L2 of the channels of the first and second NMOS transistors MN1 and MN2. The voltage $V_{PTAT2}$ of the third node NP3 of Equation 12 depends on the widths W1 and W2 and the lengths L1 and L2 of the channels of the first and second NMOS transistors MN1 and MN2, and the widths W3 and W4 and the lengths L3 and L4 of the channels of the third and fourth NMOS transistors MN3 and MN4. The voltage $V_{PTAT3}$ of the fourth node NP4 of Equation 16 depends on the widths W1 and W2 and the lengths L1 and L2 of the channels of the first and second NMOS transistors MN1 and MN2, the widths W3 and W4 and the lengths L3 and L4 of the channels of the third and fourth NMOS transistors MN3 and MN4, and the widths W5 and W6 and the lengths L5 and L6 of the channels of the fifth and sixth NMOS transistors MN5 and MN6.

The reference voltage circuit 1600 of FIG. 16 may include one sub-threshold operation circuit 221, the reference voltage circuit 1500 of FIG. 15 may include two sub-threshold operation circuits 221 and 223, and the reference voltage circuit 126 of FIG. 2 may include three sub-threshold operation circuits 221, 222, and 223. For example, when it is assumed that a chip area of the reference voltage circuit 1600 of FIG. 16 is about 300 μm$^2$, the reference voltage circuit 1500 of FIG. 15 may have a chip area of about 150 μm$^2$, and the reference voltage circuit 126 of FIG. 2 may have a chip area of about 100 μm$^2$. That is, the reference voltage circuit 126 of FIG. 2 has the least chip area.

As described above, when the number of sub-threshold operation circuits 221, 222, and 223 included in each of the reference voltage circuits 126, 1500, and 1600 increases, the chip area of the reference voltage circuits 126, 1500, and 1600 may decrease. That is, the chip area may be decreased when the large transistors MN1 and MN2 of the reference voltage circuit 1600 of FIG. 16 are divided into the plurality of transistors MN1 through MN8 as shown in FIG. 2. However, the number of the sub-threshold operation circuits 221, 222, and 223 may be limited according to a target value of the reference voltage $V_{REF}$.

Figure 17:
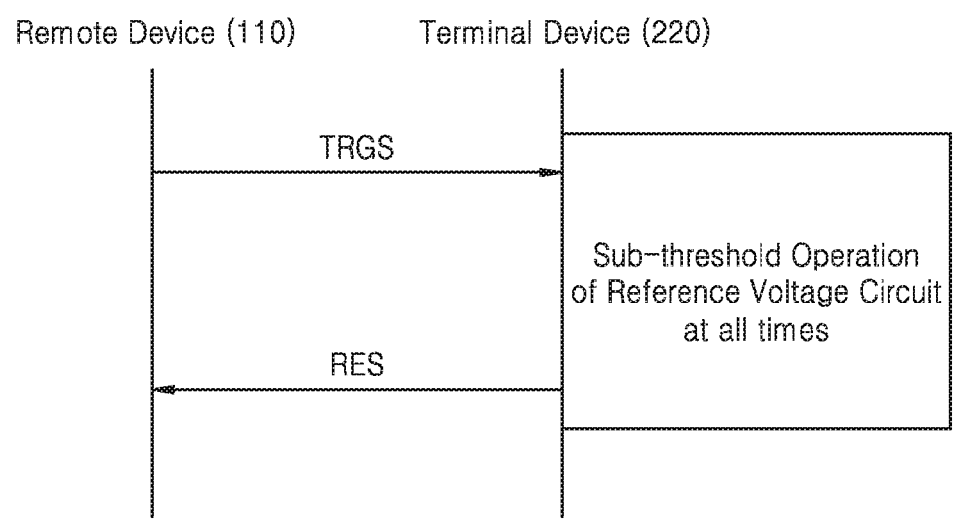
FIG. 17 is a diagram for describing an operating method of a terminal device including a reference voltage circuit according to an example embodiment.

FIG. 17 is a diagram for describing an operating method of the terminal device 120 including any one of the reference voltage circuits 126, 1400, 1500, and 1600, according to an example embodiment.

Referring to FIG. 17, the terminal device 120 may communicate with the remote device 110 via the wireless communication system 100 of FIG. 1. The remote device 110 may transmit a first signal TRGS to the terminal device 120. The first signal TRGS may include a timer, a real time clock, an event, a trigger signal, etc., provided from the remote device 110.

The terminal device 120 may generate the reference voltage $V_{REF}$ by including any one of the reference voltage circuits 126, 1400, 1500, and 1600 described with reference to FIGS. 2 through 16. The reference voltage circuits 126, 1400, 1500, and 1600 may generate a regular reference voltage $V_{REF}$ by using the NMOS transistors regularly performing sub-threshold operations. The terminal device 120 may receive the first signal TRGS from the electronic module 128 driven by the regular reference voltage $V_{REF}$. The terminal device 120 may generate a second signal RES in response to the first signal TRGS and transmit the generated second signal RES to the remote device 110. The second signal RES may correspond to a location of an object, in which the terminal device 120 is mounted, a biometric signal, a status of a structure, or the like.

While example embodiments have been particularly shown and described, it will be understood that various changes in form and details may be made therein without departing from the spirit and scope of the following claims.

What is claimed is:

1. A reference voltage circuit comprising:
    a first current bias circuit comprising a first node;
    a second current bias circuit comprising a plurality of NMOS transistors and a second node, wherein the plurality of NMOS transistors comprises a first NMOS transistor and a second NMOS transistor, the first NMOS transistor is connected to the first node, and each of the plurality of NMOS transistors are connected to the second node and configured to perform a sub-threshold operation based on a first voltage of the first node so that a second voltage is generated at the second node; and
    an amplifier configured to output a reference voltage having same value as the second voltage.

2. The reference voltage circuit of claim 1, wherein the first current bias circuit is configured to generate the first voltage of the first node based on a first current having a complementary to absolute temperature (CTAT) current characteristic.

3. The reference voltage circuit of claim 1, wherein the first current bias circuit comprises a PNP bipolar transistor comprising an emitter, a base, and a collector, wherein the emitter is connected to the first node and the base and the collector are connected to a ground voltage, and
    wherein a base-emitter voltage of the PNP bipolar transistor is provided as the first voltage of the first node.

4. The reference voltage circuit of claim 1, wherein the first current bias circuit comprises a diode comprising an anode, to which the first node is connected, and a cathode, to which a ground voltage is connected, and
    wherein a forward direction voltage of the diode is provided as the first voltage of the first node.

5. The reference voltage circuit of claim 1, wherein the amplifier is further configured to generate an output current having a same value as a current flowing in the first current bias circuit.

6. The reference voltage circuit of claim 1, wherein a first current path comprises the second node, and
    wherein the amplifier comprises a second current path comprising a third node, which is symmetrical to the second node and which is an output node of the reference voltage circuit and outputs the reference voltage.

7. The reference voltage circuit of claim 1, wherein the second current bias circuit is configured to generate the second voltage based on a current having a proportional to absolute temperature (PTAT) characteristic.

8. The reference voltage circuit of claim 1, wherein the first NMOS transistor comprises a first NMOS transistor gate, to which the first node is connected, a first NMOS transistor drain, to which a power voltage is connected, and a first NMOS transistor source, and
    wherein the second NMOS transistor comprises a second NMOS transistor gate, a second NMOS transistor drain, and a second NMOS transistor source, to which a ground voltage is connected, wherein the first NMOS transistor source is connected to the second NMOS transistor gate and the second NMOS transistor drain.

9. The reference voltage circuit of claim 8, wherein a connection node between the first NMOS transistor and the second NMOS transistor is the second node and outputs the second voltage.

10. The reference voltage circuit of claim 8, wherein the second current bias circuit further comprises:
    a third NMOS transistor comprising a third NMOS transistor gate, to which the second NMOS transistor gate and the second NMOS transistor drain, a third NMOS transistor drain, to which the power voltage is connected, and a third NMOS transistor source, and
    a fourth NMOS transistor comprising a fourth NMOS transistor gate and a fourth NMOS transistor drain, and a fourth NMOS transistor source, to which the ground voltage is connected, wherein the third NMOS transistor source is connected to the fourth NMOS transistor gate and the fourth NMOS transistor drain.

11. The reference voltage circuit of claim 10, wherein the second node is between the third NMOS transistor and the fourth NMOS transistor.

12. The reference voltage circuit of claim 10, wherein the second current bias circuit further comprises:

a fifth NMOS transistor comprising a fifth NMOS transistor gate, to which the fourth NMOS transistor gate and the fourth NMOS transistor drain are connected, a fifth NMOS transistor drain, to which the amplifier is connected, and a fifth NMOS transistor source; and a sixth NMOS transistor comprising a sixth NMOS transistor gate and a sixth NMOS transistor drain, and a sixth NMOS transistor source to which the ground voltage is connected, wherein the fifth NMOS transistor source is connected to the sixth NMOS transistor gate and the sixth NMOS transistor drain, and wherein the second node is between the fifth NMOS transistor and the sixth NMOS transistor.

13. The reference voltage circuit of claim 12, wherein the amplifier comprises:

a first PMOS transistor comprising a first PMOS transistor source, to which the power voltage is connected, a first PMOS transistor drain, to which the fifth NMOS transistor drain is connected, and a first PMOS transistor gate;

a second PMOS transistor comprising a second PMOS transistor source, to which the power voltage is connected, a second PMOS transistor gate and a second PMOS transistor drain, wherein the first PMOS transistor gate is connected to the second PMOS transistor gate and the second PMOS transistor drain;

a seventh NMOS transistor comprising a seventh NMOS transistor gate, to which the fourth NMOS transistor gate and the fourth NMOS transistor drain are connected, a seventh NMOS transistor drain, to which the second PMOS transistor drain is connected, and a seventh NMOS transistor source; and an eighth NMOS transistor comprising an eighth NMOS transistor drain, to which the seventh NMOS transistor source is connected, an eighth NMOS transistor source, to which the ground voltage is connected, and an eighth NMOS transistor gate, to which the reference voltage is generated.

14. The reference voltage circuit of claim 13, wherein the amplifier further comprises:

a third PMOS transistor comprising a third PMOS transistor source, to which the power voltage is connected, a third PMOS transistor gate, to which the fifth NMOS transistor drain is connected, and a third PMOS transistor drain; and a resistor connected between the third PMOS transistor drain and the ground voltage.

15. The reference voltage circuit of claim 14, wherein the first current bias circuit further comprises a fourth PMOS transistor comprising a fourth PMOS transistor source, to which the power voltage is connected, a fourth PMOS transistor gate, to which the fifth NMOS transistor drain is connected, and a fourth PMOS transistor drain, to which the first node is connected, and wherein a third PMOS transistor current flowing through the third PMOS transistor has a same value as a fourth PMOS transistor current flowing through the fourth PMOS transistor.

16. A terminal device comprising:

a communicator configured to receive a first signal via a wireless communication network and transmit a second signal corresponding to the first signal via the wireless communication network; and a reference voltage circuit configured to be driven by a power voltage, generate a reference voltage and apply the reference voltage to the communicator, wherein the reference voltage circuit comprises:

a first current bias circuit comprising a first node;

a second current bias circuit comprising a plurality of NMOS transistors and a second node, wherein the plurality of NMOS transistors comprises a first NMOS transistor and a second NMOS transistor, the first NMOS transistor is connected to the first node, and the plurality of NMOS transistors are connected to the second node and configured to perform a sub-threshold operation according to a first voltage of the first node to generate a second voltage at the second node; and an amplifier configured to output the reference voltage having a same value as the second voltage.

17. The terminal device of claim 16, further comprising a power supply configured to supply the power voltage.

18. The terminal device of claim 16, wherein the terminal device is configured to be physically implanted in a structure or a living subject.

19. The terminal device of claim 16, wherein the first current bias circuit is configured to generate the first voltage based on a first current having a complementary to absolute temperature (CTAT) characteristic, and wherein the second current bias circuit is configured to generate the second voltage based on a second current having a proportional to absolute temperature (PTAT) characteristic.

20. The terminal device of claim 16, wherein the amplifier is further configured to generate an output current having a same value as a current flowing in the first current bias circuit.

* * * * *